US008554697B2

(12) United States Patent
Claus et al.

(10) Patent No.: US 8,554,697 B2
(45) Date of Patent: Oct. 8, 2013

(54) SELF-LEARNING ENGINE FOR THE REFINEMENT AND OPTIMIZATION OF SURGICAL SETTINGS

(75) Inventors: Michael J. Claus, Newport Coast, CA (US); Mark E. Steen, Santa Ana, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 571 days.

(21) Appl. No.: 12/776,236

(22) Filed: May 7, 2010

(65) Prior Publication Data

US 2010/0287127 A1 Nov. 11, 2010

Related U.S. Application Data

(60) Provisional application No. 61/176,822, filed on May 8, 2009.

(51) Int. Cl.
G06F 15/18 (2006.01)

(52) U.S. Cl.
USPC .......................................................... 706/12

(58) Field of Classification Search
USPC .......................................................... 706/12
See application file for complete search history.

(56) References Cited

U.S. PATENT DOCUMENTS

| 5,997,528 | A * | 12/1999 | Bisch et al. ........................ 606/1 |
| 7,670,330 | B2 * | 3/2010 | Claus et al. .................... 604/521 |
| 7,730,362 | B2 * | 6/2010 | Claus et al. .................... 714/47.2 |
| 7,785,316 | B2 * | 8/2010 | Claus et al. .................... 604/521 |
| 7,846,126 | B2 * | 12/2010 | Steen et al. ....................... 604/28 |
| 7,921,017 | B2 * | 4/2011 | Claus et al. .................... 704/275 |
| 8,194,949 | B2 * | 6/2012 | Claus ............................ 382/128 |
| 8,287,523 | B2 * | 10/2012 | Wong et al. ....................... 606/1 |
| 8,312,098 | B2 * | 11/2012 | Claus et al. .................... 709/208 |
| 8,424,362 | B2 * | 4/2013 | Hajishah et al. ............... 73/1.58 |
| 8,425,452 | B2 * | 4/2013 | Claus et al. ..................... 604/35 |
| 8,430,841 | B2 * | 4/2013 | Claus et al. ..................... 604/35 |
| 2006/0270913 | A1 | 11/2006 | Todd |
| 2009/0005712 | A1 | 1/2009 | Raney |
| 2009/0118663 | A1 | 5/2009 | Rockley et al. |

FOREIGN PATENT DOCUMENTS

| WO | WO2005092047 A2 | 10/2005 |
| WO | WO2008031010 A2 | 3/2008 |

OTHER PUBLICATIONS

International Search Report for Application No. PCT/US2010/034114, mailed on Nov. 15, 2010, 4 pages.

* cited by examiner

Primary Examiner — Michael B Holmes
(74) Attorney, Agent, or Firm — Abbott Medical Optics Inc.

(57) ABSTRACT

The present invention pertains to a system (or engine) that monitors a system's performance during a surgery, analyzes that performance, and makes recommendations to the user/surgeon for changes in his settings and/or programs that will result in more effective and time-efficient surgeries. Further, the system may comprise one or more components, including, but not limited to, a user preference filter, a surgical circumstances filter, a surgical instrument, a real time data collection module, and an analysis module.

39 Claims, 7 Drawing Sheets

SELF-LEARNING ENGINE FOR THE REFINEMENT AND OPTIMIZATION OF SURGICAL SETTINGS

TECHNICAL FIELD OF THE INVENTION

The present invention generally relates to a self-learning system and method for customizing user programs in a surgical system, namely a phacoemulsification system.

BACKGROUND OF THE INVENTION

Phacoemulsification (hereinafter, "phaco") surgery has been successfully employed in the treatment of certain ocular problems, such as cataract surgery, including removal of a cataract-damaged lens and implanting an artificial intraocular lens. Phaco surgery typically involves removal of the cataract-damaged lens and may utilize a small incision at the edge of the cornea. Through the small incision, the surgeon then creates an opening in the capsule, i.e. membrane that encapsulates the lens.

Next, the surgeon may insert an ultrasonic probe, incorporated within the phaco handpiece, through the opening in the cornea and capsule accessing the damaged lens. The handpiece's ultrasonic actuated tip emulsifies the damaged lens sufficient to be evacuated by the handpiece. After the damaged natural lens is completely removed, the handpiece tip is withdrawn from the eye. The surgeon may now implant an intraocular lens into the space made available in the capsule.

As may be appreciated, the flow of fluid to and from a patient through a fluid infusion or extraction system and power control of the phaco handpiece is critical to the procedure performed. Different medically recognized techniques have been utilized for the lens removal portion of the surgery. Among these, one popular technique is a simultaneous combination of phaco, irrigation and aspiration using a single handpiece. Another technique is bimanual phaco, with separation of the phacoemulsification tip/aspiration handpiece from the infusion/second instrument handpiece. This method includes making the incision, inserting the handheld surgical implement to emulsify the cataract or eye lens. Simultaneously with this emulsification, the handpiece provides fluid for irrigation of the emulsified lens and vacuum for aspiration of the emulsified and inserted fluids.

Manufacturers of surgical systems typically provide their products with "recommended" or "default" settings. These settings are intended to provide acceptable performance of the instrument over a very wide variety of surgical conditions, thus enabling surgeons to utilize the system effectively without gaining an in-depth understanding of the system design. While this approach prevents the most blatant issues associated with inappropriate parameter settings, in most cases it does not result in the most efficient and time effective adjustment of the settings.

Many manufacturers also rely upon highly skilled "technical specialists" that can observe a surgeon utilizing, and subsequently can then tailor the settings to optimize the surgeon's performance. Typically, during this process, a technical specialist will offer a certain amount of input into the training concerning the design and performance of the system. The surgeon then becomes more able to adjust his own settings in the future. This approach has several drawbacks. First, the approach can be time consuming and expensive because it may take several days of operating room time for a technical specialist and a surgeon to agree on the ideal settings. Second, the approach is inconsistent because each technical specialist and surgeon may have a slightly different approach to the problem, or a slightly different concept of the "ideal" settings. Finally, technical specialist must be highly trained and as such, the number of technical specialist is limited.

The present invention not only solves the foregoing problems, but provides an effective and efficient way of customizing programs based on a user's preferences and performance. The present invention provides a system that monitors and analyzes performance of surgical systems, and recommends changes to a user's settings and/or programs.

SUMMARY OF THE INVENTION

The present invention pertains to a system, comprising a component, wherein the component is selected from the group consisting of an analysis module, a user preference filter, a surgical circumstances filter, and a real time data collection module, wherein the analysis module comprises one or more algorithms and is configured to use one or more base settings, one or more user settings, and/or one or more real time instrument data to recommend one or more changes to the one or more base settings and/or one or more user settings, wherein the user preference filter comprises one or more algorithms and is configured to use a default programs database and user preferences to generate one or more base settings, wherein the surgical circumstances filter comprises one or more algorithms and is configured to use one or more selected from the group consisting of: one or more base settings, one or more recommended changes, and one or more surgical/patient circumstances to generate one or more user settings, and wherein the real time data collection module is configured to monitor and/or record the real time data collected using the surgical instrument and store the real time data in a real time instrument data database.

One embodiment of the present invention pertains to a system comprising an analysis module, wherein the analysis module is configured to use one or more base settings, one or more user settings, and/or one or more real time instrument data to recommend one or more changes to the one or more base settings and/or one or more surgeon settings.

In another embodiment, the present invention pertains to a system comprising: a user preference filter, wherein the user preference filter is configured to use a default programs database and user preferences to generate one or more base settings; and an analysis module, wherein the analysis module is configured to use the one or more base settings to recommend one or more changes to the one or more base settings.

In yet another embodiment, the present invention pertains to a system comprising: a surgical circumstances filter, wherein the surgical circumstances filter is configured to use one or more selected from the group consisting of: one or more base settings and one or more surgical/patient circumstances to generate one or more user settings; and an analysis module, wherein the analysis module is configured to use the one or more user settings to recommend one or more changes to the one or more base settings and the one or more surgical/patient circumstances.

In yet another embodiment, the present invention pertains to a system comprising: a surgical instrument, wherein the surgical instrument is configured to operate based on one or more user settings; a real time data collection module, wherein the real time data collection module is configured to monitor and/or record the real time data collected using the surgical instrument and store the real time data in a real time instrument data database; and an analysis module, wherein the analysis module is configured to use the real time instrument data database comprising real time instrument data, one or more base settings, and/or the one or more user settings to recommend one or more changes to one or more base settings and/or the one or more user settings.

According to another embodiment, the present invention pertains to a system comprising: a user preference filter, wherein the user preference filter is configured to use a default programs database and user preferences to generate one or more base settings; a surgical circumstances filter, wherein the surgical circumstances filter is configured to use the one or more selected from the group consisting of: the one or more base settings and one or more surgical/patient circumstances to generate one or more user settings; a surgical instrument, wherein the surgical instrument is configured to operate based on the one or more user settings; a real time data collection module, wherein the real time data collection module is configured to monitor and/or record the real time data collected using the surgical instrument and store the real time data in a real time instrument data database; and an analysis module, wherein the analysis module is configured to use the real time instrument data database comprising real time instrument data, the one or more base settings, and/or the one or more user settings to recommend one or more changes to the one or more base settings and/or the one or more user settings. The surgical instrument may be an ophthalmic surgical instrument and the ophthalmic surgical instrument may be a phacoemulsification instrument.

The present invention also may include a method for customizing user programs in a surgical system, comprising: inputting into a user preference filter one or more default programs from a default programs database and one or more user preferences; generating one or more base settings from the user preference filter; inputting into a surgical circumstances filter one or more selected from the group consisting of the one or more base settings and one or more surgical/patient circumstances; generating one or more user settings from the surgical circumstances filter; applying the one or more user settings to a surgical instrument; monitoring real time data using a real time data collection module; recording the real time data in the real time data collection module; generating a real time instrument data database based on the real time data; imputing into an analysis module one or more selected from the group consisting of the real time data, the one or more base settings, and the one or more user settings; and generating recommended changes to the one or more base settings and/or the one or more surgical circumstance algorithms. The surgical instrument may be an ophthalmic surgical instrument and the ophthalmic surgical instrument may be a phacoemulsification instrument.

To better understand the nature and advanced of the invention, reference should now be made to the following description and the accompanying figures. It is to be understood, however, that each of the figures is provided for the purposes of illustration only and is not intended as a definition of the limits of the scope of the present invention.

BRIEF DESCRIPTION OF THE DRAWINGS

The present invention is best understood with reference to the following detailed description of the invention and the drawings in which.

DETAILED DESCRIPTION OF THE INVENTION

Reference will now be made in detail to embodiments of the invention, examples of which are illustrated in the accompanying drawings. While the invention will be described in conjunction with the embodiments, it will be understood that they are not intended to limit the invention to those embodiments. On the contrary, the invention is intended to cover alternatives, modifications, and equivalents, which may be included within the spirit and scope of the invention as defined by the appended claims.

The present invention pertains to a system (or engine) that monitors a system's performance during a surgery, analyzes that performance, and makes recommendations to the user/surgeon for changes in his settings, programs, and/or equipment that will result in more effective and time-efficient surgeries. The recommendations may be employed automatically during and/or after a procedure or employed upon user selection.

Figure 1:
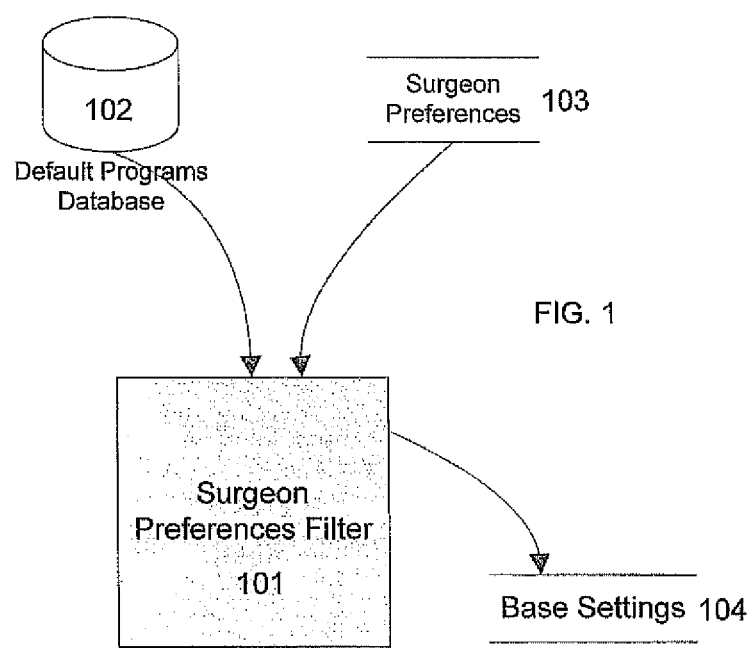
FIG. 1 is a block diagram illustrating a component (surgeon preference filter) of the system of the present invention.

FIG. 1 illustrates a block diagram of a component of the present invention, namely surgeon preference filter 101. System 100 comprises a default programs database 102 that provides for basic system settings to operate a surgical instrument. Default programs database 102 may be set/installed by a manufacturer of the surgical instrument and/or added to a surgical instrument by a user or manufacturer. System 100 also comprises surgeon preference filter 101 that may accept one or more surgeon (user) preferences 103 inputted by a surgeon and inputted from default programs database 102. Surgeon preferences 103 may include, but is not limited to, programs, settings, features, etc. Surgeon preferences filter 101 functions to produce a set of base settings 104 which are appropriate to a given surgeon under a wide variety of surgical circumstances. System 100 may accept as input a variety of surgeon preferences including, but not limited to, handpiece type (longitudinal, non-longitudinal, etc.), phaco tip/sleeve style and size; pump preferences (venturi/peristaltic); surgical technique (divide and conquer, chop, carousel, etc.); foot pedal preferences (single linear, dual liner, switch settings, feedback options, etc.); sound preferences; and sub-mode preferences, which may include, but is not limited to specific features of the foregoing preferences. Default programs database 102 may contain a large number of surgeon preferences 103 and/or base settings 104, each categorized by it relative efficiency when used with the various parameters described in surgeon preferences 103. Based upon one or more surgeon preferences 103 and default program settings 114 stored in default programs database 102, system 100 may generate recommended base settings 104 that can be used as the surgeon's default program(s). Base settings 104 may only need to be established one time (although they may be updated at any time). Base settings 104 may be stored in a memory and/or database of surgeon preferences or in default programs database 102.

Surgeon preferences 103 may be analyzed and/or compared against a database of known default program settings 114. System 100 may determine the base settings contained in the database which most closely matches the specified surgeon preferences 103 via the surgeon preference filter 101, which may include one or more algorithms. The mechanism employed to determine the most closely fitting set of base settings may include least-squares regression analysis or other statistical algorithms as appropriate, however any analysis or algorithm known in the art may be employed. Furthermore, system 100 may tailor the most closely matching base settings 104 with specific algorithms for given surgeon preferences 103 that will make the resulting base settings 104 an even closer match to the specified surgeon preferences 103. The resulting base settings 104 may also be utilized by other components of the system as described herein.

Figure 2:
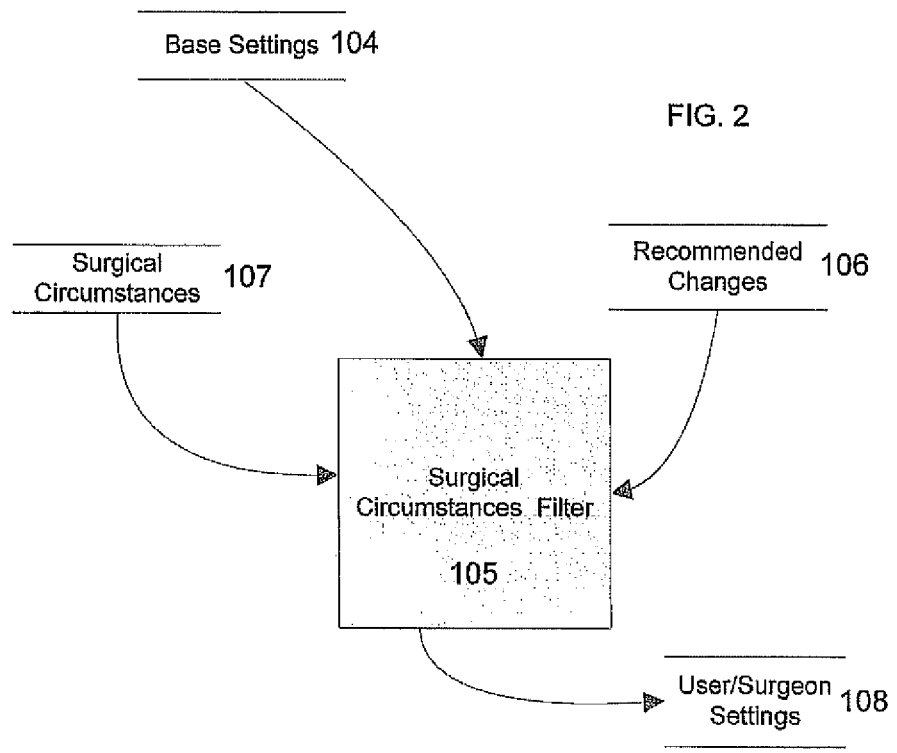
FIG. 2 is a block diagram illustrating a component (surgical circumstances filter) of the system of the present invention.

Referring to FIG. 2, another component of system 100, circumstances filter 105, is illustrated. Circumstances filter 105 is capable of accepting base settings 104, recommended changes 106, and/or surgical/patient circumstances 107. Prior to the execution of each surgical procedure, system 100 accepts surgical/patient circumstances 107. Surgical/patient circumstances 107 may include, but are not limited to, additional input about the patient, such as cataract density, shallow chamber, a floppy iris, etc. The additional input may be from an internal (e.g. internal sensors, programs, etc.) or an external source (e.g. user/surgeon input). Surgical/patient circumstances 107 may be used to adjust base settings 104 to be more appropriate for the specific circumstances of the particular surgical procedure.

Surgical circumstances filter 105 gathers a set of inputs related to a specific patient and a specific surgery to be performed. These parameters will be collected separately for each surgical case. These parameters include, but are not limited to, cataract density, anterior chamber depth and volume, patient identification information, disease states (floppy iris, loose zonules, etc.), and intended IOL type.

These parameters are maintained in a data store of surgical/patient circumstances 107. Surgical circumstances filter 105 may analyze surgical/patient circumstances 107 parameters and adjust base settings 104 to an instrument program more appropriate for the particular surgical circumstances. For example, it might adjust maximum phaco power, chamber automated stabilization environment (CASE) settings/parameters, maximum vacuum and flow rates up/down depending upon the cataract density, pulse shape and/or width, duty cycle, tip movement (e.g. torsional, transverse, longitudinal, etc.), occlusion threshold, pump ramp, movement of the foot pedal (linear, panel, or non-zero start), and/or any other setting known in the art. To aid in its function, surgical circumstances filter 105 may draw upon additional parameters maintained in an optional database of algorithms located within surgical circumstances filter 105 or external to surgical circumstances filter 105. For example the module might determine that the maximum phaco power needs to be adjusted upwards if the cataract density is high. The actual amount of adjustment (a % of the value in base settings 104 and/or user settings 108) might be drawn from one or more algorithms of surgical circumstances filter 105. CASE is an occlusion mode advancement that corrects the vacuum in the anterior chamber of an eye by anticipating breaks in the occlusion. For additional information, see co-assigned U.S. application Ser. No. 11/086,508 filed on Mar. 21, 2005 and U.S. application Ser. No. 11/401,529 filed on Apr. 10, 2006; the entirety of each is hereby incorporated by reference.

The output from surgical circumstances filter 105 is user settings 108. These settings are used to guide the phaco system during the surgery.

Any of the filters and/or modules described herein may comprise one or more algorithms. For example, algorithms that may be utilized with the present invention include, but are not limited to, adjusting maximum phaco power up/down in response to cataract density; adjusting vacuum and flow settings up/down in response to increases or decreases in anterior chamber depth; lower maximum vacuum settings in response to known Flomax® use or other floppy iris conditions; increasing/decreasing CASE up/time parameter in response to cataract density increases/decreases; enabling/disabling non-longitudinal phaco technology in particular sub-modes depending upon the cataract density; enabling/disabling the occlusion mode technology, or adjusting the occlusion threshold up/down, depending upon cataract density; adjusting CASE mode parameters (up time, up threshold, CASE vacuum, down threshold) up/down in response to cataract density, intraoperative floppy iris syndrome resulting from tamsulosin (Flomax®) use and/or other floppy iris conditions; and adjusting maximum vacuum up/down in response to anterior chamber depth.

As the surgeon performs the surgery, the phaco system interprets user settings 108, the position of the surgeon's foot pedal, and/or other inputs into the system. The actual values of all the instrument parameters at any given moment in time are a function of the mix of these inputs into the phaco system.

During the procedure, system 100 monitors and records in real time various instrument parameters including, but not limited to, phaco power, phaco modes, vacuum levels, flow rate, etc. These actual instrument parameters can be analyzed and compared to the settings that were used. Recommendations can then be made for adjustments to the base settings that will result in faster, safer and/or more efficient surgeries in the future.

Figure 3:
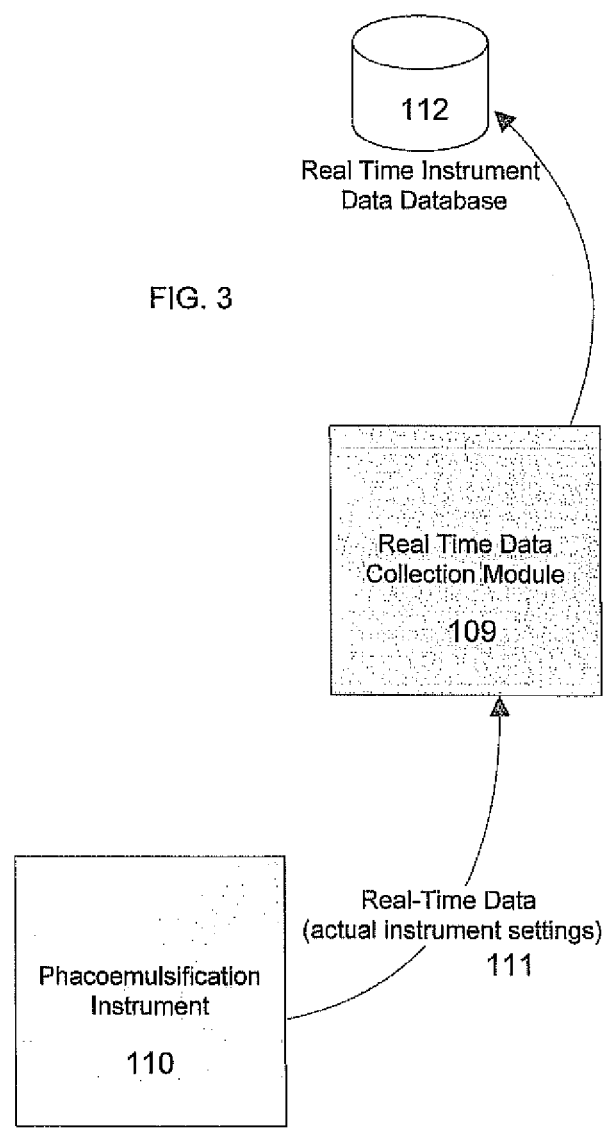
FIG. 3 is a block diagram illustrating a component (real time data collection module) of the system of the present invention.

Another component of system 100 is real time data collection module 109. This component is shown in FIG. 3. Real time data collection module 109 monitors the performance of the phaco system during surgery, and records an accurate history of actual instrument settings (real time data) 111 used for phaco instrument 110. Settings 111 are stored as a sequence of settings frames. Each frame contains settings 111 that were in use during one particular instant of the surgery. The actual rate at which frames are taken and stored may vary—depending upon the complexity of the surgery, user preferences and/or other circumstances. It is expected that frames will be stored at least every 100 ms, and could be stored as often as every 1 ms. Frames will be stored together with the date and time at which they were collected.

The actual data to be collected and stored in the frames may include, but is not limited to, actual and maximum vacuum; actual and maximum phaco power; actual and maximum flow; actual and maximum diathermy power; actual and maximum vitrectomy cut rate; bottle height; irrigation pressure; foot pedal zone; foot pedal position (pitch and yaw); occlusion status; CASE status; phaco system errors and warnings; pump type (venturi/peristaltic/combination); current active major mode; current active sub-mode; current effective phaco time (EPT) (effective phaco time is the total amount of time at 100% power during a procedure), non-longitudinal EPT (also known as Ellips™ EPT or amplitude), average phaco power throughout a procedure (AVG) and ultrasound time (UST) timers (which is the amount of time ultrasound is used in the eye); phaco power delivery mode and settings; non-longitudinal handpiece status (on/off/duty cycle); WhiteStar® system status (on/off/duty cycle); vacuum settings (linear/panel/non-zero start); and flow settings (linear/panel).

It may not be necessary to collect all data in every frame. There could be different frame rates for different pieces of data.

The collected instrument settings (real time data (frames)) 111 are stored in real time instrument data database 112. Real time instrument data database 112 may contain all of the real-time data collected by phaco instrument 110 and may be easily indexed and searched to extract any particular piece of data. Real time instrument data database 112 may contain real-time data collected from multiple surgeries, from multiple surgeons and/or from multiple phaco systems.

Real time data 111 inputted into real time data collection module 109 may be displayed on a graphical user interface (GUI) as the real time data 111 is collected and/or after one or more surgical procedures. Real time data 111 stored in real time instrument database 112 may also be displayed on a GUI during or after one or more surgical procedures. The real time data 111 displayed on the GUI may be selected by the user, including how the real time data 111 is displayed, such as, but not limited to, based on the average between multiple surgeries, based on a period of time, etc.

Figure 6:
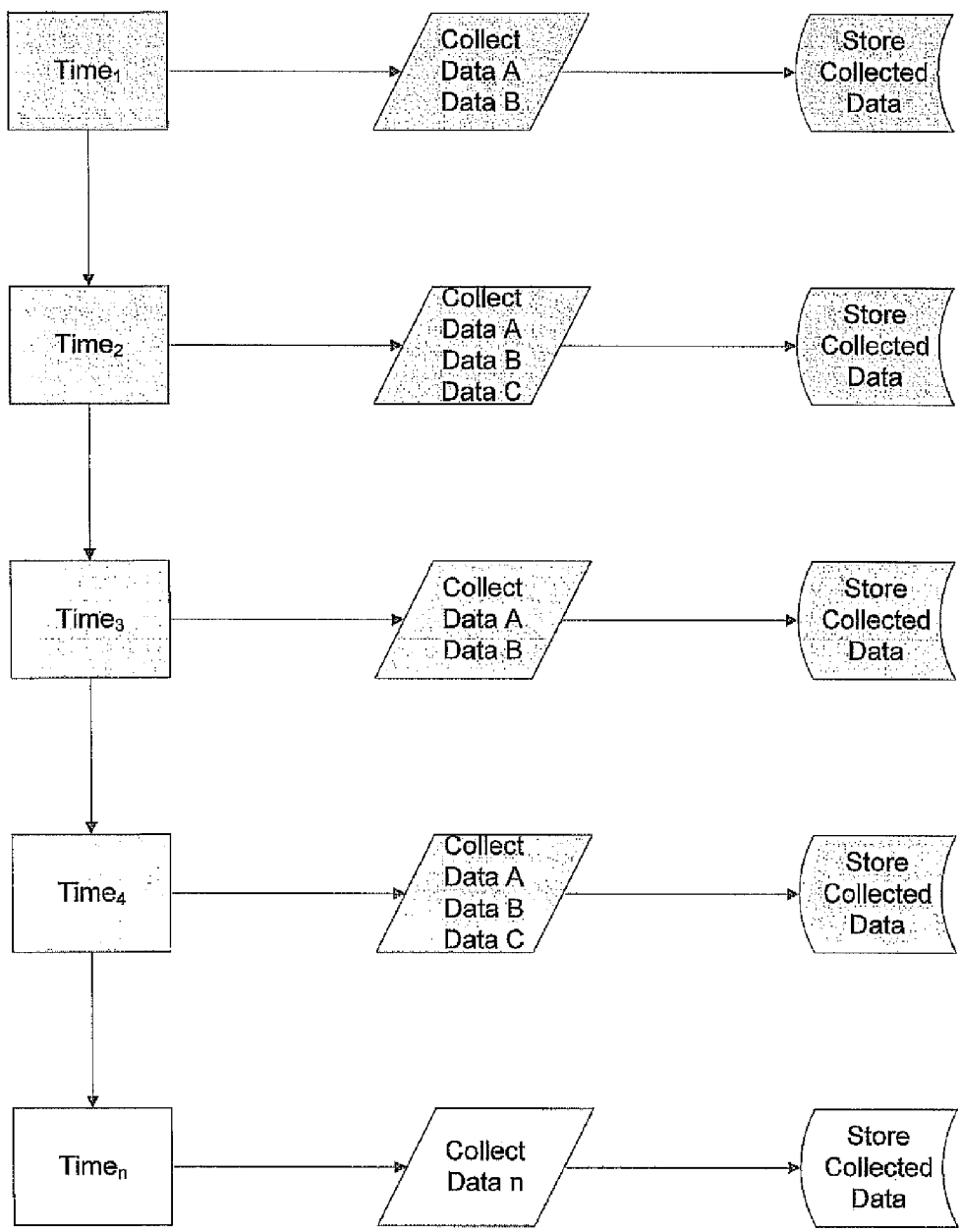
FIG. 6 is a block diagram illustrating an embodiment of the real time data collection module.

According to an embodiment, at time intervals $t_1, t_2, t_3, \ldots t_n$, the actual vacuum and actual phaco power may be collected by real time data collection module 109 and stored in real time instrument data database 112. In addition to the foregoing time intervals or as an alternative, the actual flow and pump type may be collected at intervals $t_a, t_b, t_c, \ldots t_x$ by real time data collection module 109 and stored in real time instrument data database 112. Any combination of data, including but not limited to, actual, maximum, and minimum data of specific parameters, may be collected and stored during the surgery at any time interval. The time intervals may be set and/or programmed by each user or may be preprogrammed time intervals that are set as a default. See FIG. 6 for a flowchart of the process of real time data collection module 109.

Figure 4:
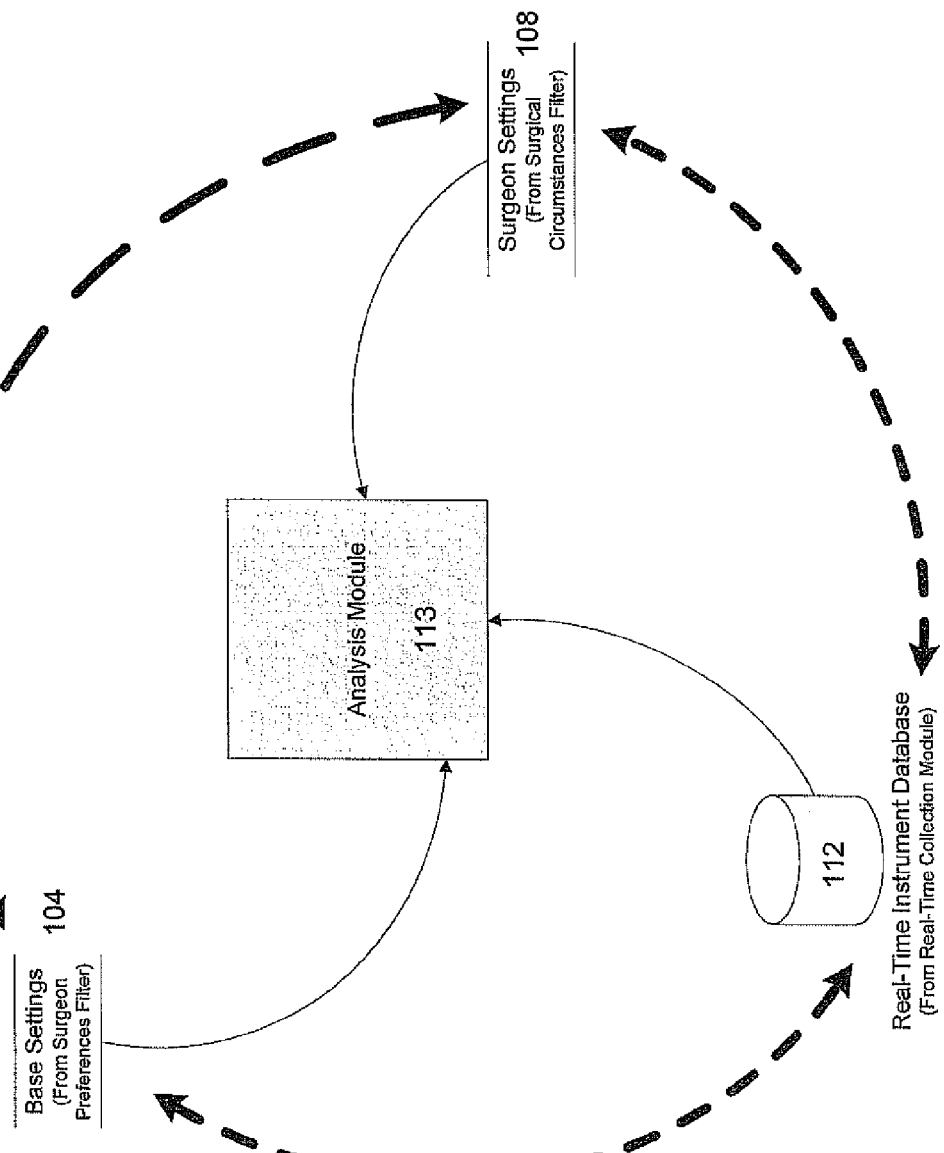
FIG. 4 is a block diagram illustrating a component (analysis module) of the system of the present invention.
Figure 7:
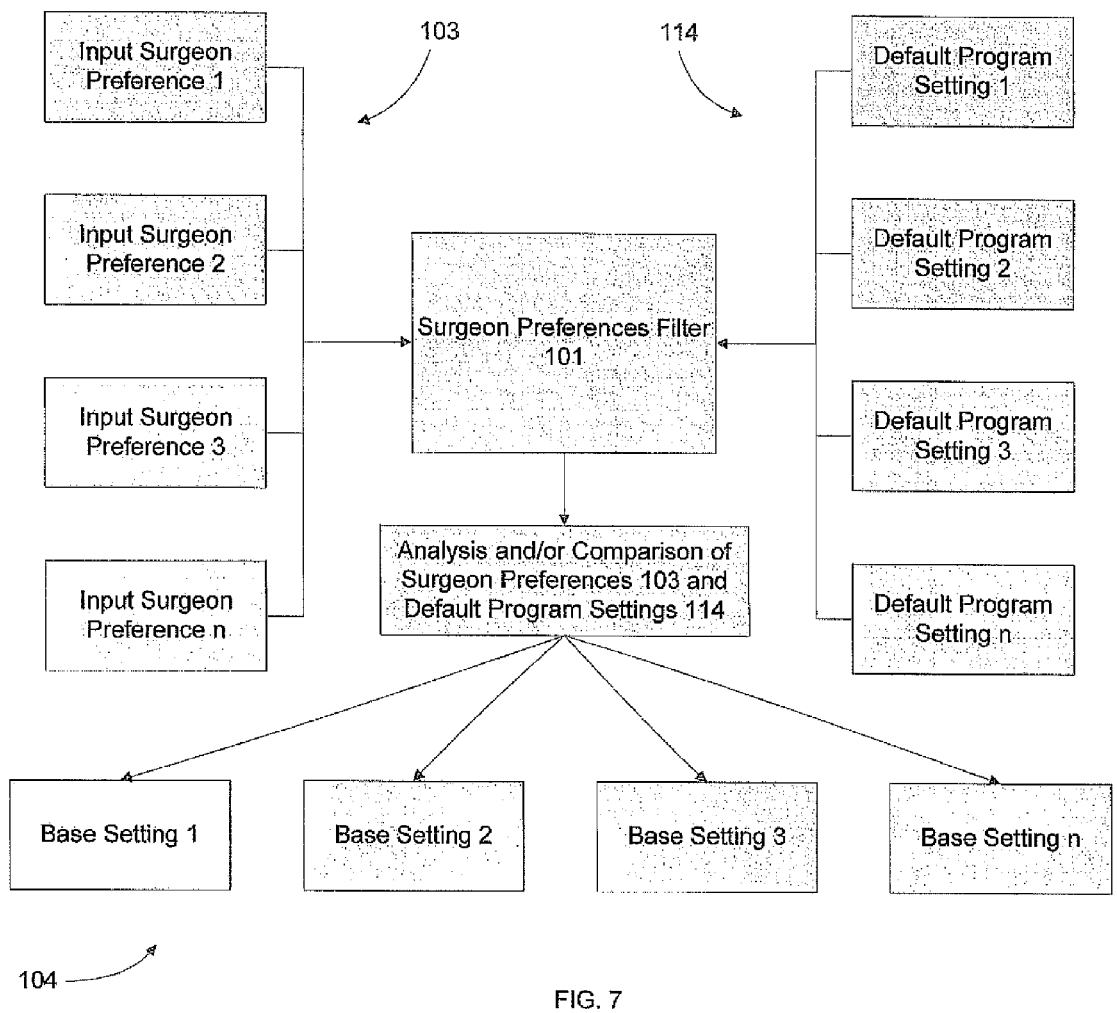
FIG. 7 is a block diagram illustrating an embodiment of the surgeon preferences filter.

A component of system 100 is analysis module 113 shown in FIG. 4. Analysis module 113 may analyze the collected instrument settings (real time data) 111 from real time instrument data database 112. It may compare real time instrument data database 112 with current surgeon preferences 103, surgical/patient circumstances 107, and/or base settings 104. As a result of this analysis, it will provide recommended changes 106 for changing or adjusting base settings 104 and/or user settings 108. See FIG. 7 for a flowchart of the process of surgeon preferences filter 101.

The analysis may take many forms, including, but not limited to analyzing the number of occlusions and CASE events during the surgery; analyzing the number of times there was a vacuum break from the non-CASE vacuum level; analyzing the average phaco power compared to the programmed maximum phaco power; analyzing the average vacuum (occluded and unoccluded) compared to the programmed maximum vacuum; analyzing the use of the foot pedal and the surgeon's use of the linear modes for power, vacuum and flow; analyzing percentage of time spent in the various modes and sub-modes; and analyzing the balance of vacuum and irrigation during the case.

Analysis module 113 may accept input from one or more sources, including, but not limited to, base settings 104, user settings 108, and real time instrument data database 112. According to an embodiment, from one of these sources, analysis module 113 can make inferences/recommendations regarding changes to the source to enhance the effectiveness of the surgical procedure and/or make the surgical procedure more efficient. For example, from base settings 108, analysis module 113 can make recommendations regarding improvements to base settings 108 for a more effective and/or efficient surgery. According to another embodiment, from any two of these sources, system 100 can make inferences/recommendations regarding the third. For example, from user settings 108 and instrument settings (real time data) 111 from real time instrument data database 112, analysis module 113 can make recommendations regarding improvements to base settings 104 for a more effective and/or efficient surgery. From base settings 104 and real time data 111, system 100 may make assumptions about the surgeon settings and the associated surgical circumstances. From base settings 104 and user settings 108, system 100 may make assumptions about expected format of real time data 111.

Analysis module 113 may function over a wide variety of time scales. For example, it could be used to make some basic recommendations after only a few minutes of surgery. Alternatively, it could be utilized to analyze surgical data following many days or weeks of surgery. It is expected that the accuracy and validity of the analysis engines recommendations will improve as the amount of available data for analysis increases.

Any component in the system of the present invention as described herein may operate alone or in combination with any other component(s). For example, surgeon preference filter 101 may be the only component of system 100 operating for a period of time. Thus, only base settings 104 will be created. Also envisioned is a combination of components such as, surgical circumstances filter 105 and real time data collection module 109. When both components are operating, real time data 111 will be collected and stored and surgeon settings 108 will be created based upon one or more of base settings 104, surgical circumstances 107, and recommended changes 106. Additional components may be added to the system of the present invention to assist with customizing a surgical procedure, including but not limited to components relating to capsulotomy, vitrectomy, and video analysis of a procedure (e.g. image analysis which is used to control various settings). Any adjustments and/or changes to any parameter may be made automatically with or without user/surgeon input.

Figure 5:
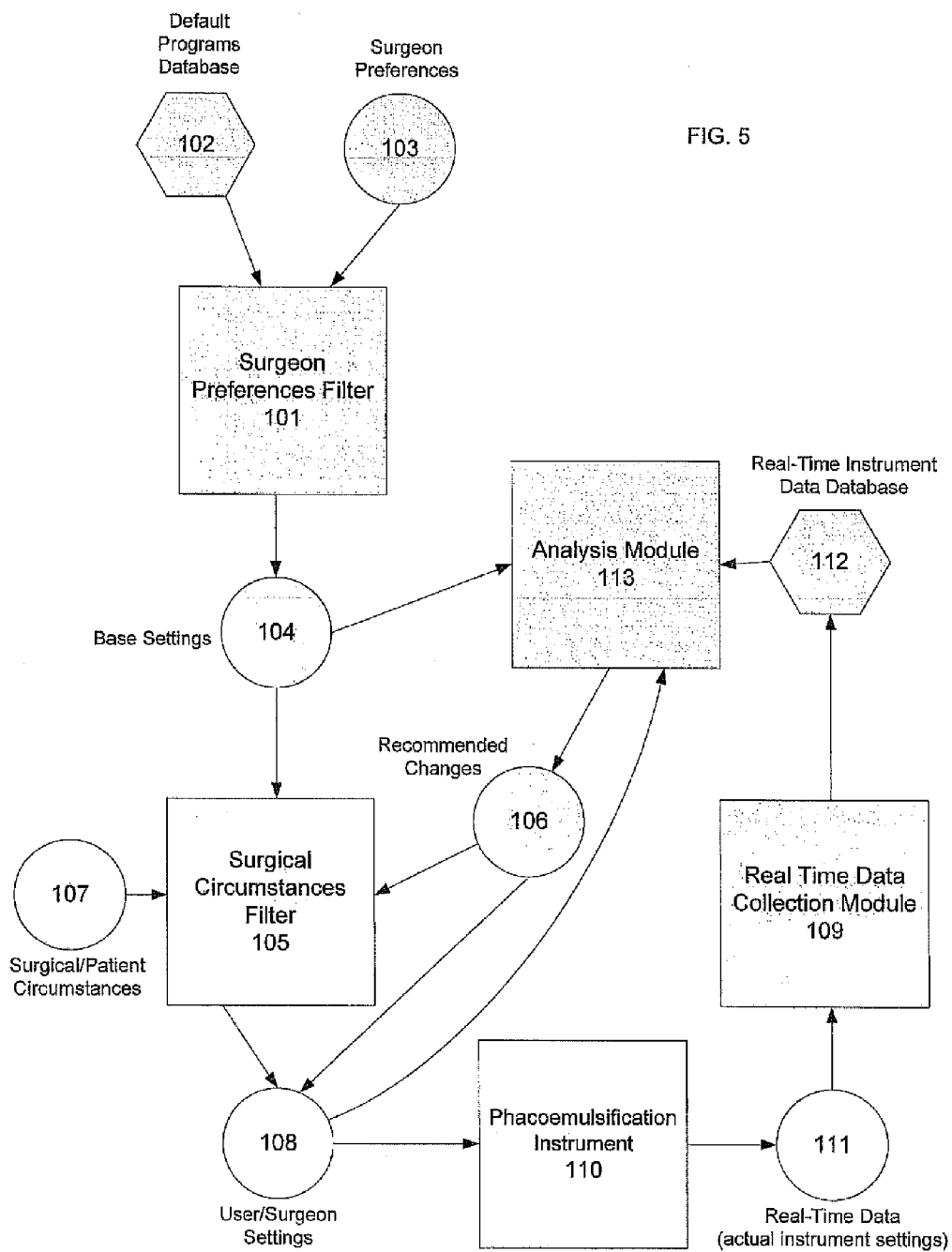
FIG. 5 is a block diagram illustrating various components of the system of the present invention.

FIG. 5 illustrates a block diagram of system 100 defining various databases, data stores, and functional modules that comprise system 100, and how they may function together. Although the various databases are shown as individual databases, one or more of the databases discussed herein may be a single database or housed in a single database. The single database may be made up of sub-databases. Surgeon preferences 103, base settings 104, surgical/patient circumstances 107, user/surgeon settings 108, recommended changes 106, and real-time data 111 may be stored in a single database or in any one of the other specific databases discussed herein.

The system of the present invention offers a number of advantages over the current approaches, including:

a. Allowing for an easy selection of a variety of default base settings tailored to a particular surgeon's technique and preferences. These default settings are likely to be more closely optimized for that surgeon than a single "default" setting utilized by all surgeons.

b. Allowing the default settings to be easily tailored to specific surgical conditions—such as cataract density, etc. These adjustments can greatly improve the efficiency of the settings for a particular case.

c. Providing a consistent algorithm(s) for recommending changes to the default programs. It no longer depends upon the specific training of individual Technical Specialists.

d. It would be continuously available on any system on which it is installed. Thus, it no longer depends upon the availability of an expensive, highly trained Technical Specialist.

e. It can implement proprietary algorithms, which would eliminate the concern that a Technical Specialist moving to a competitive company will take competitive information/intellectual property with them.

f. It can be reused at any time. For example, if the surgeon wishes to update his technique or change his preferences he may do so.

According to an embodiment, the frequency with which the data is collected and stored may vary depending upon a number of factors, including, but not limited to, the particular phase of the surgery (i.e. phaco mode my require more frequent data than diathermy mode); the capability of the hardware on which the system is implemented; and the preferences of the users. The most likely implementation will collect data every 100 milliseconds, but might realistically be as often as every 1 millisecond or even faster depending upon the capabilities of the underlying hardware.

System 100 may be implemented to perform analysis in a variety of ways at the request of the user. The user may ask system 100 to perform an analysis and make recommendations based upon any number of conditions including, but not limited to, all cases within a particular time frame—hours, days, weeks, etc.; over a particular number of cases; by a particular surgeon; and/or matching a set of surgical circumstances. Analysis might also be done on any combination of these criteria—for example analyze all cases performed by a particular doctor between July 1 and September 30 with a cataract density of 3 or higher.

The system recommendations could be automatically implemented into the base settings, or the system could make only recommendations. Such recommendations would require approval by the surgeon or the tech specialist before they would be implemented. The system may be utilized to make settings changes interoperatively as the surgery proceeds or after the completion of the surgery or multiple surgeries. The user/surgeon may also have the option of running or not running particular filters and/or modules or algorithms of the filters and/or modules. The user/surgeon may also have the option of accepting and/or rejecting various recommendations from the system. The user/surgeon may also lock particular base settings, user/surgeon settings, etc., e.g. vacuum, power, etc.

Also, the system may allow input of surgical/patient circumstances 107 by the user to make choices based upon icons that look like slit lamp images, Pentacam® images or other diagnostic images that would be familiar to a typical cataract surgeon.

The present invention may be extended to include settings, circumstances and analysis appropriate for vitreo-retinal and other posterior segment surgeries. Analysis may be targeted to optimize certain aspects of the surgery—for example to minimize the amount of phaco energy, or to maximize the use of the CASE mode All references cited herein are hereby incorporated by reference in their entirety including any references cited therein.

Although the present invention has been described in terms of specific embodiments, changes and modifications can be carried out without departing from the scope of the invention which is intended to be limited only by the scope of the claims.

The invention claimed is:

1. A system, comprising:
a component, wherein the component is selected from the group consisting of an analysis module, a user preference filter, a surgical circumstances filter, and a real time data collection module,
wherein the analysis module comprises one or more algorithms and is configured to use one or more base settings, one or more user settings, and/or one or more real time instrument data to recommend one or more changes to the one or more base settings and/or one or more user settings,
wherein the user preference filter comprises one or more algorithms and is configured to use a default programs database and user preferences to generate one or more base settings,
wherein the surgical circumstances filter comprises one or more algorithms and is configured to use one or more selected from the group consisting of: one or more base settings, one or more recommended changes, and one or more surgical/patient circumstances to generate one or more user settings, and
wherein the real time data collection module is configured to monitor and/or record the real time data collected using the surgical instrument and store the real time data in a real time instrument data database.

2. A system, comprising:
an analysis module, wherein the analysis module comprises one or more algorithms and is configured to use one or more base settings, one or more user settings, and/or one or more real time instrument data to recommend one or more changes to the one or more base settings and/or one or more user settings; and
a surgical circumstances filter comprising one or more algorithms and configured to use one or more selected from the group consisting of: one or more base settings, one or more recommended changes, and one or more surgical/patient circumstances to generate one or more user settings.

3. A system, comprising:
a user preference filter, wherein the user preference filter comprises one or more algorithms and is configured to use a default programs database and user preferences to generate one or more base settings; and
a surgical circumstances filter comprising one or more algorithms and configured to use one or more selected from the group consisting of: one or more base settings, one or more recommended changes, and one or more surgical/patient circumstances to generate one or more user settings.

4. A system, comprising:
a surgical circumstances filter, wherein the surgical circumstances filter comprises one or more algorithms and is configured to use one or more selected from the group consisting of: one or more base settings, one or more recommended changes, and one or more surgical/patient circumstances to generate one or more user settings; and
an analysis module, wherein the analysis module comprises one or more algorithms and is configured to use one or more base settings, one or more user settings, and/or one or more real time instrument data to recommend one or more changes to the one or more base settings and/or one or more user settings.

5. A system, comprising:
a surgical instrument, wherein the surgical instrument is configured to operate based on one or more user settings;
a real time data collection module, wherein the real time data collection module is configured to monitor and/or record the real time data collected using the surgical instrument and store the real time data in a real time instrument data database; and
an analysis module, wherein the analysis module comprises one or more algorithms and is configured to use the real time instrument data database comprising real time instrument data, one or more base settings, and/or the one or more user settings to recommend one or more changes to one or more base settings, and/or the one or more user settings.

6. A system, comprising:
a user preference filter, wherein the user preference filter is configured to use a default programs database and user preferences to generate one or more base settings;
a surgical circumstances filter, wherein the surgical circumstances filter comprises one or more algorithms and is configured to use the one or more selected from the group consisting of: the one or more base settings and one or more surgical/patient circumstances to generate one or more user settings;
a surgical instrument, wherein the surgical instrument is configured to operate based on the one or more user settings;
a real time data collection module, wherein the real time data collection module is configured to monitor and/or record the real time data collected using the surgical instrument and store the real time data in a real time instrument data database; and
an analysis module, wherein the analysis module comprises one or more algorithms and is configured to use the real time instrument data database comprising real time instrument data, the one or more base settings, and/or the one or more user settings to recommend one or more changes to the one or more base settings and/or the one or more user settings.

7. The system of claim 6, wherein the surgical instrument is an ophthalmic surgical instrument.

8. The system of claim 7, wherein the ophthalmic surgical instrument is a phacoemulsification instrument.

9. The system of claim 6, wherein one or more user preferences is selected from the group consisting of: phacoemulsification tip style, phacoemulsification tip size, phacoemulsification sleeve style, phacoemulsification sleeve size, vacuum based pump, flow based pump, sound, foot pedal type, foot pedal settings, and surgical technique.

10. The system of claim 6, wherein the one or more surgical/patient circumstances is selected from the group consisting of: cataract density, anterior chamber depth, anterior chamber volume, patient identification, disease state, and intraocular lens type.

11. The system of claim 6, wherein the one or more algorithms is selected from the group consisting of: adjusting maximum phacoemulsification power in response to cataract density; adjusting vacuum and/or flow settings in response to increase or decreases in anterior chamber depth, lowering maximum vacuum settings in response to disease state or condition, adjusting chamber automated stabilization environment parameters in response to cataract density, enabling or disabling ultrasonic mode based on cataract density, adjusting chamber automated stabilization environment parameters in response to disease state or condition, and adjusting maximum vacuum setting in response to anterior chamber depth.

12. The system of claim 6, wherein the real time data comprises one or more selected from the group consisting of: actual vacuum level, maximum vacuum level, actual phacoemulsification power, maximum phacoemulsification power, actual flow rate, maximum flow rate, actual diathermy power, maximum diathermy power, actual vitrectomy cut rate, maximum vitrectomy cut rate, bottle height, irrigation pressure, foot pedal zone, foot pedal position, occlusion status, chamber automated stabilization environment status, system errors, system warnings, pump type, current active major mode, current active sub-mode, current effective phacoemulsification time, non-longitudinal effective phacoemulsification time, average phacoemulsification power during a procedure, amount of time ultrasound is used in an eye, phacoemulsification power delivery mode, phacoemulsification power delivery settings, handpiece duty cycle, handpiece on time, handpiece off time, ultrasonic power duty cycle, ultrasonic power on time, ultrasonic power off time, vacuum settings, and flow settings.

13. The system of claim 6, wherein the analysis module is configured to analyze one or more selected from the group consisting of: number of occlusions, number of chamber automated stabilization environment (CASE) events, number of vacuum breaks from non-CASE vacuum level, average phacoemulsification power compared to a programmed maximum power, average vacuum compared to a programmed maximum vacuum for occlusion, average vacuum compared to a programmed maximum vacuum for no occlusion, use of a foot pedal, use of linear modes for power, vacuum, and/or flow, percentage of time spent in various modes and/or sub-modes, and balance of vacuum and irrigation during a procedure.

14. A method for customizing user programs in a surgical system, comprising:
inputting into a user preference filter one or more default program settings from a default programs database and one or more user preferences;
generating one or more base settings from the user preference filter;
inputting into a surgical circumstances filter one or more selected from the group consisting of the one or more base settings and one or more surgical/patient circumstances;
generating one or more user settings from the surgical circumstances filter;
applying the one or more user settings to a surgical instrument;
monitoring real time data using a real time data collection module;
recording the real time data in the real time data collection module;
generating a real time instrument data database based on the real time data;
imputing into an analysis module one or more selected from the group consisting of the real time data, the one or more base settings, and the one or more user settings; and
generating recommended changes to at least one program employing the one or more base settings, the one or more user settings, and/or the one or more surgical/patient circumstances.

15. The method of claim 14, wherein the surgical instrument is an ophthalmic surgical instrument.

16. The method of claim 15, wherein the ophthalmic surgical instrument is a phacoemulsification instrument.

17. The method of claim 14, wherein one or more user preferences is selected from the group consisting of: phacoemulsification tip style, phacoemulsification tip size, phacoemulsification sleeve style, phacoemulsification sleeve size, vacuum based pump, flow based pump, sound, foot pedal type, foot pedal settings, and surgical technique.

18. The method of claim 14, wherein the one or more surgical/patient circumstances is selected from the group consisting of: cataract density, anterior chamber depth, anterior chamber volume, patient identification, disease state, and intraocular lens type.

19. The method of claim 14, wherein the real time data comprises one or more selected from the group consisting of: actual vacuum level, maximum vacuum level, actual phacoemulsification power, maximum phacoemulsification power, actual flow rate, maximum flow rate, actual diathermy power, maximum diathermy power, actual vitrectomy cut rate, maximum vitrectomy cut rate, bottle height, irrigation pressure, foot pedal zone, foot pedal position, occlusion status, chamber automated stabilization environment status, system errors, system warnings, pump type, current active major mode, current active sub-mode, current effective phacoemulsification time, non-longitudinal effective phacoemulsification time, average phacoemulsification power during a procedure, amount of time ultrasound is used in an eye, phacoemulsification power delivery mode, phacoemulsification power delivery settings, handpiece duty cycle, handpiece on time, handpiece off time, ultrasonic power duty cycle, ultrasonic power on time, ultrasonic power off time, vacuum settings, and flow settings.

20. The method of claim 14, wherein the analysis module is configured to analyze one or more selected from the group consisting of: number of occlusions, number of chamber automated stabilization environment (CASE) events, number of vacuum breaks from non-CASE vacuum level, average phacoemulsification power compared to a programmed maximum power, average vacuum compared to a programmed maximum vacuum for occlusion, average vacuum compared to a programmed maximum vacuum for no occlusion, use of a foot pedal, use of linear modes for power, vacuum, and/or flow, percentage of time spend in various modes and/or sub-modes, and balance of vacuum and irrigation during a procedure.

21. The method of claim 14, wherein the default program settings comprise one or more selected from the group consisting of stored base settings and stored user preferences.

22. A non-transitory computer-readable medium having computer-executable instructions for performing a method, comprising:
inputting into a user preference filter one or more default program settings from a default programs database and one or more user preferences;
generating one or more base settings from the user preference filter;
inputting into a surgical circumstances filter one or more selected from the group consisting of the one or more base settings and one or more surgical/patient circumstances;
generating one or more user settings from the surgical circumstances filter;
applying the one or more user settings to a surgical instrument;
monitoring real time data using a real time data collection module;
recording the real time data in the real time data collection module;
generating a real time instrument data database based on the real time data;
imputing into an analysis module one or more selected from the group consisting of the real time data, the one or more base settings, and the one or more user settings; and
generating recommended changes to at least one program employing the one or more base settings, the one or more user settings, and/or the one or more surgical/patient circumstances.

23. The non-transitory computer-readable medium of claim 22, wherein the surgical instrument is an ophthalmic surgical instrument.

24. The non-transitory computer-readable medium of claim 23, wherein the ophthalmic surgical instrument is a phacoemulsification instrument.

25. The non-transitory computer-readable medium of claim 22, wherein one or more user preferences is selected from the group consisting of: phacoemulsification tip style, phacoemulsification tip size, phacoemulsification sleeve style, phacoemulsification sleeve size, vacuum based pump, flow based pump, sound, foot pedal type, foot pedal settings, and surgical technique.

26. The non-transitory computer-readable medium of claim 22, wherein the one or more surgical/patient circumstances is selected from the group consisting of: cataract density, anterior chamber depth, anterior chamber volume, patient identification, disease state, and intraocular lens type.

27. The non-transitory computer-readable medium of claim 22, wherein the real time data comprises one or more selected from the group consisting of: actual vacuum level, maximum vacuum level, actual phacoemulsification power, maximum phacoemulsification power, actual flow rate, maximum flow rate, actual diathermy power, maximum diathermy power, actual vitrectomy cut rate, maximum vitrectomy cut rate, bottle height, irrigation pressure, foot pedal zone, foot pedal position, occlusion status, chamber automated stabilization environment status, system errors, system warnings, pump type, current active major mode, current active sub-mode, current effective phacoemulsification time, non-longitudinal effective phacoemulsification time, average phacoemulsification power during a procedure, amount of time ultrasound is used in an eye, phacoemulsification power delivery mode, phacoemulsification power delivery settings, handpiece duty cycle, handpiece on time, handpiece off time, ultrasonic power duty cycle, ultrasonic power on time, ultrasonic power off time, vacuum settings, and flow settings.

28. The non-transitory computer-readable medium of claim 22, wherein the analysis module is configured to analyze one or more selected from the group consisting of: number of occlusions, number of chamber automated stabilization environment (CASE) events, number of vacuum breaks from non-CASE vacuum level, average phacoemulsification power compared to a programmed maximum power, average vacuum compared to a programmed maximum vacuum for occlusion, average vacuum compared to a programmed maximum vacuum for no occlusion, use of a foot pedal, use of linear modes for power, vacuum, and/or flow, percentage of time spend in various modes and/or sub-modes, and balance of vacuum and irrigation during a procedure.

29. The non-transitory computer-readable medium of claim 22, wherein the default program settings comprise one or more selected from the group consisting of stored base settings and stored user preferences.

30. A non-transitory computer-readable medium having stored thereon a data structure, comprising:
a user preference filter, wherein the user preference filter is configured to use a default programs database and user preferences to generate one or more base settings;
a surgical circumstances filter, wherein the surgical circumstances filter is configured to use the one or more selected from the group consisting of: the one or more base settings and one or more surgical/patient circumstances to generate one or more user settings;
a real time data collection module, wherein the real time data collection module is configured to monitor and/or record the real time data collected using a surgical instrument and store the real time data in a real time instrument data database; and an analysis module, wherein the analysis module is configured to use the real time instrument data database comprising real time instrument data, the one or more base settings, and/or one or more user settings to recommend one or more changes to at least one program employing the one or more base settings, the one or more surgical/patient circumstances, and/or the one or more user settings.

31. The non-transitory computer-readable medium of claim 30, wherein the surgical instrument is an ophthalmic surgical instrument.

32. The non-transitory computer-readable medium of claim 31, wherein the ophthalmic surgical instrument is a phacoemulsification instrument.

33. The non-transitory computer-readable medium of claim 30, wherein one or more user preferences is selected from the group consisting of: phacoemulsification tip style, phacoemulsification tip size, phacoemulsification sleeve style, phacoemulsification sleeve size, vacuum based pump, flow based pump, sound, foot pedal type, foot pedal settings, and surgical technique.

34. The non-transitory computer-readable medium of claim 30, wherein the one or more surgical/patient circumstances is selected from the group consisting of: cataract density, anterior chamber depth, anterior chamber volume, patient identification, disease state, and intraocular lens type.

35. The non-transitory computer-readable medium of claim 30, wherein the real time data comprises one or more selected from the group consisting of: actual vacuum level, maximum vacuum level, actual phacoemulsification power, maximum phacoemulsification power, actual flow rate, maximum flow rate, actual diathermy power, maximum diathermy power, actual vitrectomy cut rate, maximum vitrectomy cut rate, bottle height, irrigation pressure, foot pedal zone, foot pedal position, occlusion status, chamber automated stabilization environment status, system errors, system warnings, pump type, current active major mode, current active sub-mode, current effective phacoemulsification time, non-longitudinal effective phacoemulsification time, average phacoemulsification power during a procedure, amount of time ultrasound is used in an eye, phacoemulsification power delivery mode, phacoemulsification power delivery settings, handpiece duty cycle, handpiece on time, handpiece off time, ultrasonic power duty cycle, ultrasonic power on time, ultrasonic power off time, vacuum settings, and flow settings.

36. The non-transitory computer-readable medium of claim 30, wherein the analysis module is configured to analyze one or more selected from the group consisting of: number of occlusions, number of chamber automated stabilization environment (CASE) events, number of vacuum breaks from non-CASE vacuum level, average phacoemulsification power compared to a programmed maximum power, average vacuum compared to a programmed maximum vacuum for occlusion, average vacuum compared to a programmed maximum vacuum for no occlusion, use of a foot pedal, use of linear modes for power, vacuum, and/or flow, percentage of time spend in various modes and/or sub-modes, and balance of vacuum and irrigation during a procedure.

37. A system, comprising:
a user preference filter, wherein the user preference filter comprises one or more algorithms and is configured to use a default programs database and user preferences to generate one or more base settings; and
a surgical circumstances filter comprising one or more algorithms and configured to use one or more selected from the group consisting of: one or more base settings, one or more recommended changes, and one or more surgical/patient circumstances to generate one or more user settings.

38. A system, comprising:
a surgical circumstances filter, wherein the surgical circumstances filter comprises one or more algorithms and is configured to use one or more selected from the group consisting of: one or more base settings, one or more recommended changes, and one or more surgical/patient circumstances to generate one or more user settings;
wherein the one or more surgical/patient circumstances is selected from the group consisting of: cataract density, anterior chamber depth, anterior chamber volume, patient identification, disease state, and intraocular lens type.

39. A system, comprising: a real time data collection module, wherein the real time data collection module is configured to monitor and/or record the real time data collected using the surgical instrument and store the real time data in a real time instrument data database; and
a surgical circumstances filter comprising one or more algorithms and configured to use one or more selected from the group consisting of: one or more base settings, one or more recommended changes, and one or more surgical/patient circumstances to generate one or more user settings.

* * * * *